(12) United States Patent
Inoue

(10) Patent No.: US 6,967,211 B2
(45) Date of Patent: Nov. 22, 2005

(54) REMEDIAL AGENT FOR CHRONIC ARTICULAR RHEUMATISM

(75) Inventor: Naoki Inoue, Nagaokakyo (JP)

(73) Assignee: Nippon Shinyaku Co. Ltd. (JP)

( * ) Notice: Subject to any disclaimer, the term of this patent is extended or adjusted under 35 U.S.C. 154(b) by 0 days.

(21) Appl. No.: 10/472,432

(22) PCT Filed: Apr. 9, 2002

(86) PCT No.: PCT/JP02/03524

§ 371 (c)(1),
(2), (4) Date: Sep. 19, 2003

(87) PCT Pub. No.: WO02/087578

PCT Pub. Date: Nov. 7, 2002

(65) Prior Publication Data

US 2004/0116481 A1 Jun. 17, 2004

(51) Int. Cl.$^7$ ................... A61K 31/44; C07D 211/70
(52) U.S. Cl. ................. 514/351; 514/348; 514/349; 514/350; 546/334
(58) Field of Search .................. 514/351, 348, 514/349, 350, 353, 357; 546/334, 308, 337

(56) References Cited

U.S. PATENT DOCUMENTS 5,972,976 A * 10/1999 Hidaka et al. .............. 514/357

FOREIGN PATENT DOCUMENTS

| CN | 1253135 | | 5/2000 |
|---|---|---|---|
| EP | 0 606 046 A1 | | 12/1993 |
| EP | 0 754 682 A1 | | 1/1997 |
| EP | 1 238 974 A1 | | 12/2000 |
| EP | 1 113 000 A1 | | 8/2001 |
| EP | 1 174 427 A1 | | 2/2002 |
| JP | 2001-261649 | * | 9/2001 |
| WO | WO 99/53094 | * | 10/1999 |
| WO | 2000064875 | * | 11/2000 |

OTHER PUBLICATIONS

Tanaka et. al., "Isolation of cDNAs Encoding Cellular Drug–Binding Proteins Using a Novel Expression Cloning Procedure: Drug–Western", Molecular Pharmacology, 55: 356–363 (1999).*

* cited by examiner

Primary Examiner—Cecilia J. Tsang
Assistant Examiner—Binta Robinson
(74) Attorney, Agent, or Firm—Greenberg Traurig LLP; Eugene C. Rzucidlo

(57) ABSTRACT

The present invention relates to an excellent remedial agent for chronic rheumatoid arthritis, comprising an aminostilbazole derivative represented by the following formula [1] or a salt thereof as an active ingredient:

A-B-D-E    [1]

Wherein A represents heteroaryl or an oxide thereof, B represents ethenylene, D represents phenylene, E represents the formula: —N(R)SO$_2$—G [wherein G represents phenyl, R represents hydrogen, alkyl, or —COR$^0$ (R$^0$ represents alkyl, alkoxy, aryloxy, 5- to 6-membered heteroaryl, heteroarylmethyl, aminoalkylene or cyclicaminoalkylene) or the like].

8 Claims, No Drawings

REMEDIAL AGENT FOR CHRONIC ARTICULAR RHEUMATISM

TECHNICAL FIELD

The present invention relates to a remedy for chronic rheumatoid arthritis.

BACKGROUND ART

Chronic rheumatoid arthritis is an intractable autoimmune disease which is associated with swelling, inflammation, rigidity and pain of the joint and exhibits a clinical picture of generalized polyarthritis. That is, it is a generalized disease in which the living body recognizes self as nonself based on recognition defect of self and nonself, and attacks the self-tissue to cause abnormal immune response, resulting in inflammation of the connective tissue.

A major protein constituting the connective tissue is collagen and at least five kinds (I, II, III, IV and V types) collagens are found in homoiotherm. The joint contains joint cartilage which contains type II collagen as a main component. Major diseased site of chronic rheumatoid arthritis is synovial tissue where infiltration of lymphocyte consisting mainly of T-cells is recognized. Also it has conventionally been known that clone, which specifically reacts with type II collagen, exists in CD4+T cells which infiltrated into synovial membrane. As an antigen capable of producing self-reactive T-cells, proteoglycan, adenovirus, EB virus and heat shock protein are known, in addition to type II collagen. Among them, type II collagen is considered to be one of most prominent self-antigens because it is a main component of the cartilage and exists in the joint. Chronic rheumatoid arthritis provokes the breakage of cartilage and bone while repeating remission and aggravation to cause structural deformation of the peripheral joint.

As a drug therapy for chronic rheumatoid arthritis, an anti-inflammatory steroid (for example, prednisolone), non-steroidal anti-inflammatory drugs (for example, indomethacin, aspirin), an immunosuppressive agent (for example, cyclosporin A, tacrolimus (FK506), methotrexate, cyclophosphamide, azathioprine) and a disease-modifying antirheumatic drug (for example, gold salt preparation) are used. Although the anti-inflammatory agent can alleviate pain and swelling by controlling inflammation, it is hard to suppress the progression of this disease. It is considered that, among the above immunosuppressive agents, cyclosporin A and tacrolimus exert an immunosuppression effect by suppressing the production of IL-2 from T-cells. Although a mechanism of the action of the disease-modifying antirheumatic drug has never been elucidated, it has an effect for sedation and remission of this disease.

As described above, any drugs merely relieve the symptom and delay the progression of the disease and also revoke side effects involved in administration for a long period, and thus these drugs are not satisfactory drugs. Therefore, it is strongly required to develop a novel remedy for chronic rheumatoid arthritis.

It is known that the aminostilbazole derivative of the present invention has an intense anticancer activity and very low toxicity (International Publication WO95/27699).

DISCLOSURE OF THE INVENTION

An object of the present invention is to provide a novel remedy for chronicrheumatoid arthritis.

From the above-described point of view, the present inventors have carried out researches on various compounds in order to find a compound which suppresses chronic rheumatoid arthritis. As a result, we have found an inhibitory effect of aminostilbazole derivatives (hereinafter sometimes referred to as the compounds of the present invention) represented by the following general formula [1] on type II collagen-induced arthritis. Thus, the present invention has been completed.

The present invention relates to a remedy for chronic rheumatoid arthritis, comprising a compound represented by the following general formula [1] or a salt thereof as an active ingredient:

A-B-D-E         [1]

[wherein A represents optionally substituted heteroaryl or an oxide thereof, B represents optionally substituted ethenylene, D represents optionally substituted phenylene, E represents the following formula:

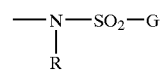

(wherein G represents optionally substituted phenyl, R represents (1) hydrogen, (2) optionally substituted alkyl, (3) optionally substituted alkenyl, (4) alkynyl, or (5) —COR⁰, R⁰ represents alkyl, alkoxy, aryloxy, optionally substituted heteroaryl, optionally substituted heteroarylmethyl, or the following formula:

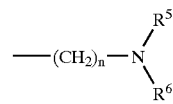

wherein n represents an integer of 1 to 5, $R^5$ and $R^6$ are the same or different and each represents hydrogen, alkyl, hydroxyalkyl or aminoalkyl, or $R^5$ and $R^6$ are taken together with adjacent nitrogen atoms as —NR⁵(R⁶) to form optionally substituted cyclic amino, and cyclic amino may have one oxygen, sulfur or nitrogen atom, as an annular atom, in addition to nitrogen atom)].

Preferably, the present invention relates to a remedy for chronic rheumatoid arthritis, comprising the compounds of the present invention or the salt thereof as an active ingredient, wherein A is optionally substituted pyridyl or 1-oxide pyridyl, B is non-substituted ethenylene, D is non-substituted or aminoalkoxy-substituted 1,2-phenylene, R of —N(R)—SO₂—G as E is alkyl which may be substituted with a substituent selected from the group consisting of halogen, amino, monoalkylamino, dialkylamino, morpholino, alkoxy, hydroxy, cyano, the formula: —CONR¹R² (wherein $R^1$ and $R^2$ are the same or different and each represents hydrogen, hydroxy, alkyl, alkoxy, cycloalkyl, cycloalkyloxy, aryl, aryloxy, aralkyl, aralkyloxy, cycloalkylalkyl, cycloalkylalkyloxy, or tetrahydrofuranyloxy), and the formula: —SO₂NR³R⁴ (wherein R³ and R⁴ are the same or different and each represents hydrogen or alkyl), alkenyl which may be substituted with halogen, or —COR⁰, R⁰ is alkyl, cyclic amino alkyl or dialkylaminoalkyl, and G is 4-alkoxyphenyl.

More preferably, the present invention relates to a remedy for chronic rheumatoid arthritis, comprising the compounds of present invention or the salt thereof as an active ingredient, wherein A is non-substituted 4-pyridyl or 1-oxide-4-pyridyl, B is ethenylene of a non-substituted trans form, D is non-substituted or aminoalkoxy-substituted 1,2-phenylene, R of —N(R)—SO₂—G as E is hydrogen, hydroxyalkyl or —COR⁰, R⁰ is alkyl, morpholinoalkyl or dialkylaminoalkyl, and G is 4-methoxyphenyl.

A feature of the present invention resides in the fact that the compound of the formula [1] has an inhibitory effect of chronic rheumatoid arthritis and is useful for the treatment of chronic rheumatoid arthritis. It has never been described in the document and also has never been known that the above compound has such an effect.

The present invention will be described in detail below.

Terms used in the present specification and definitions of the respective substituents are as follows.

The term "remedy for chronic rheumatoid arthritis" as used herein refers to a drug which alleviates pain of the joint to relieve inflammation of the joint, or a drug which maintains or repairs a joint function to prevent the breakage of bone and cartilage.

Examples of "heteroaryl" may include 5- to 6-membered heteroaryl having 1 to 2 nitrogen atoms as an annular atom. Such a heteroaryl may have 1 to 2 substituents at any positions and examples of the substituent may include halogen, alkyl, alkoxy, hydroxy, aminoalkyl and the like. Examples of "heteroaryl" as A may include 6-membered heteroaryl, for example, 2-pyridyl, 3-pyridyl, 4-pyridyl, 2-pyrimidinyl, 4-pyrimidinyl, 5-pyrimidinyl, 3-pyridazinyl, 4-pyridazinyl and pyrazinyl. Among them, non-substituted 4-pyridyl is preferable. Examples of the heteroaryl moiety of "heteroaryl" and "heteroarylmethyl" as R⁰ may include 5- to 6-membered heteroaryl, for example, 2-pyridyl, 3-pyridyl, 4-pyridyl, 2-pyrimidinyl, 4-pyrimidinyl, 5-pyrimidinyl, 3-pyridazinyl, 4-pyridazinyl, 1-imidazolyl, 2-imidazolyl and 4-imidazoly. Among them, pyridyl is preferable.

"Ethenylene" may have a substituent on the respective carbon atoms and examples of the substituent may include cyano, bromo, alkyl and the like. Among them, non-substituted ethenylene is preferable.

Examples of "phenylene" may include 1,2-phenylene, 1,3-phenylene and 1,4-phenylene. Such a phenylene group may have 1 to 2 substituents at any positions and examples of the substituent may include hydroxy, halogen, amino, alkyl, alkoxy, aminoalkoxy and the like. Non-substituted or aminoalkoxy-substituted 1,2-phenylene is preferable.

"Phenyl" may have 1 to 2 substituents and examples of the substituent may include hydroxy, alkoxy and the like. Among them, alkoxy-substituted phenyl is preferable and 4-methoxyphenyl is particularly preferable.

Examples of "halogen" may include fluorine, chlorine, bromine, iodine and the like.

Examples of "alkyl" may include straight-chain or branched-chain alkyl having 1 to 6 carbon atoms, for example, methyl, ethyl, n-propyl, isopropyl, n-butyl, isobutyl, sec-butyl, tert-butyl, n-pentyl, isopentyl, n-hexyl, isohexyl and the like. Among them, alkyl having 1 to 4 carbon atoms is preferable and methyl is particularly preferable. Alkyl as R may be substituted with a substituent selected from the group consisting of halogen, amino, monoalkylamino, dialkylamino, morpholino, alkoxy, hydroxy, cyano, the formula: —CONR¹R² (wherein R¹ and R² are the same or different and each represents hydrogen, hydroxy, alkyl, alkoxy, cycloalkyl, cycloalkyloxy, aryl, aryloxy, aralkyl, aralkyloxy, cycloalkylalkyl, cycloalkylalkyloxy, or tetrahydrofuranyloxy) and the formula: —SO₂NR³R⁴ (wherein R³ and R⁴ are the same or different and each represents hydrogen or alkyl).

Examples of the alkyl moiety of "hydroxyalkyl", "monoalkylamino", "dialkylamino", "aminoalkyl", "cycloalkylalkyl" and "cycloalkylalkyloxy" may include "alkyl" described above.

Examples of "alkoxy" may include straight-chain or branched-chain alkoxy having 1 to 6 carbon atoms, for example, methoxy, ethoxy, n-propoxy, isopropoxy, n-butoxy, isobutoxy, sec-butoxy, tert-butoxy, n-pentyloxy, isopentyloxy, n-hexyloxy and isohexyloxy. Among them, alkoxy having 1 to 4 carbon atoms is preferable and methoxy is particularly preferable.

Examples of the alkoxy moiety of "aminoalkoxy" may include "alkoxy" described above.

Examples of "aryloxy" may include optionally substituted aryloxy having 6 to 10 carbon atoms, for example, phenoxy, 1-naphthyloxy and 2-naphthyloxy. Among them, phenoxy is preferable. Examples of the substituent may include alkyl, halogen, hydroxy, alkoxy and the like.

Examples of "alkenyl" may include straight-chain or branched-chain alkenyl having 2 to 6 carbon atoms, for example, vinyl, 1-propenyl, 2-propenyl, isopropenyl, 2-butenyl, 3-butenyl, isobutenyl, metallyl, prenyl, isoprenyl and 1,1-dimethylallyl. Among them, alkenyl having 2 to 4 carbon atoms is preferable. "Alkenyl" as R may be substituted with halogen.

Examples of "alkynyl" may include straight-chain or branched-chain alkynyl having 2 to 6 carbon atoms, for example, ethynyl, 1-propynyl, 2-propynyl, 2-butynyl, 3-butynyl and 3-methyl-2-butynyl. Particularly, alkynyl having 2 to 4 carbon atoms is preferable.

In alkylene represented by "—(CH₂)ₙ—", hydrogen atom may be substituted with one amino or alkyl at any positions.

Examples of "cyclic amino" may include 5- to 8-membered cyclic amino, for example, pyrrolidin-1-yl, piperidino, hexamethyleneimino, tetrahydropyridin-1-yl, octahydroazocin-1-yl, piperazin-1-yl, homopiperazin-1-yl, morpholino and thiomorpholino. Such a cyclic amino may have 1 to 2 substituents selected from the group consisting of alkyl, alkenyl, alkynyl, aryl, aralkyl and heterocycle group having a nitrogen atom at any positions. Among them, 5- to 6-membered cyclic amino is preferable, and piperazin-1-yl substituted with pyridyl, non-substituted pyrrolidin-1-yl, piperidino or morpholino is preferable.

Examples of "aryl" may include aryl having 6 to 10 carbon atoms, for example, phenyl, 1-naphthyl and 2-naphthyl.

Examples of "aralkyl" may include aralkyl having 7 to 8 carbon atoms, for example, benzyl and phenethyl.

Examples of the aralkyl moiety of "aralkyloxy" may include those described above.

Examples of "heterocycle having a nitrogen atom" may include cyclic amino and heteroaryl described above. Such a heterocycle may have 1 to 2 substituents selected from the group consisting of alkyl, amino, hydroxy and oxo.

Examples of "cycloalkyl" may include cycloalkyl having 3 to 8 carbon atoms, for example, cyclopropyl, cyclobutyl, cyclopentyl, cyclohexyl, cycloheptyl and cyclooctyl.

Examples of the cycloalkyl moiety of "cycloalkyloxy", "cycloalkylalkyl" and "cycloalkylalkyloxy" may include those described above.

Examples of "salt" of the compounds of the present invention may include pharmacologically acceptable salts, for example, salts with inorganic acids such as hydrochloric acid, sulfuric acid, nitric acid, phosphoric acid, hydrofluoric acid and hydrobromic acid, and salts with organic acids such as acetic acid, tartaric acid, lactic acid, citric acid, fumaric acid, maleic acid, succinic acid, methanesulfonic acid, ethanesulfonic acid, benzenesulfonic acid, toluenesulfonic acid, naphthalenesulfonic acid and camphorsulfonic acid.

The compounds of the present invention may exist in cis (Z form) and trans (E form) isomers, and each isomer and a mixture thereof are also included in the present invention. Particularly, the E form is preferable.

Examples of the compounds of the present invention may include compounds of the formula [1]. Among them,
(E)-4-[2-{2-[N-acetyl-N-(4-methoxybenzenesulfonyl) amino]phenyl}ethenyl]pyridine 1-oxide,
(E)-4-[2-{2-[N-acetyl-N-(4-methoxybenzenesulfonyl) amino]phenyl}ethenyl]pyridine,
(E)-4-[2-{2-[N-(4-methoxybenzenesulfonyl)amino] phenyl}ethenyl]pyridine 1-oxide,
(E)-4-[2-{2-[N-(4-methoxybenzenesulfonyl)amino] phenyl}ethenyl]pyridine,
(E)-4-[2-{2-[N-(2-hydroxyethyl)-N-(4-methoxybenzenesulfonyl)amino]phenyl}ethenyl] pyridine 1-oxide,
(E)-4-[2-{2-[N-(2-hydroxyethyl)-N-(4-methoxybenzenesulfonyl)amino]phenyl}ethenyl] pyridine,
(E)-4-[2-{3-(2-aminoethyloxy)-2-[N-(4-methoxybenzenesulfonyl)amino]phenyl}ethenyl] pyridine, and
(E)-4-[2-{3-(2-aminoethyloxy)-2-[N-(4-methoxybenzenesulfonyl)amino]phenyl}ethenyl] pyridine 1-oxide are preferable.

The compounds of the present invention can be produced by the method described in International Publication WO95/27699, International Publication WO01/44195 or Japanese Unexamined Patent Publication No. 2001-261649, or a version thereof.

When the compounds of the present invention are administered as a remedy for chronic rheumatoid arthritis, they can be administered to a mammal including human as they are or in a mixture with a pharmaceutically acceptable non-toxic inert carrier, for example, as a pharmaceutical composition containing the compound at a level of 0.1 to 99.5% by weight, preferably 0.5 to 90% by weight.

The carrier that can be used includes solid, semi-solid and liquid diluent, filler and other formulation auxiliaries and at least one of them is selectively employed. The pharmaceutical composition is preferably administered in a unit dosage form. The pharmaceutical composition of the present invention can be administered by the oral route, or parenterally (for example, injection or rectally). Of course, a dosage form suited for each route of administration should be used. For example, oral administration is particularly preferable.

The dosage of the compound as a remedy for chronic rheumatoid arthritis may preferably be adjusted in consideration of the patient's factors such as age, body weight, etc., charactor and severity of disease, etc., as well as the route of administration, a daily dose as an active ingredient in an adult is usually 0.1 mg to 300 mg per adult, preferably 1 mg to 100 mg per adult when given orally. In some cases, a lower dose may be sufficient or a higher dose may be required. The above-mentioned daily dosage is preferably administered once or several times as being divided into portions.

Oral administration can be carried out using a solid or liquid unit dosage form, such as a particle, powder, tablet, sugar-coated tablet, capsule, granule, suspension, liquid, syrup, drop, sublingual tablet or other dosage forms.

A particle is produced by pulverizing the compound of the present invention in to a suitable particle size. A powder can be produced by pulverizing the compound of the present invention into a suitable particle size followed by mixing with a pharmaceutical carrier, such as an edible carbohydrate including starches or mannitol, which has also been pulverized into a suitable particle size. Those that may be added if necessary are flavors, preservatives, dispersing agents, colorants, fragrances and the like.

A capsule may be produced by filling a particle or powder, which has been pulverized as described above or a granule obtained as described in the section of a tablet for example in a capsule such as a gelatin capsule. It is also possible that an additive such as a lubricant, fluidizing agent, such as colloidal silica, talc, magnesium stearate, calcium stearate or solid polyethylene glycol is mixed with the pulverized material prior to the filling procedure. The efficacy of the drug after ingestion of a capsule may be improved by adding a disintegrator or solubilizer, such as carboxymethyl cellulose, calcium carboxymethyl cellulose, low substituted hydroxypropyl cellulose, sodium croscarmellose, sodium carboxymethyl starch, calcium carbonate or sodium carbonate, may be added.

The finely pulverized powder may be suspended and dispersed in a vegetable oil, polyethylene glycol, glycerin and surfactant, and then encapsulated in a gelatin sheet, thereby obtaining a soft capsule.

A tablet can be produced by preparing a powdery composition by adding an excipient, granulating or slugging it, adding a disintegrator or lubricant thereto, and then compact into a tablet. The powdery composition can be produced by mixing an appropriately pulverized material with a diluent or base described above if necessary together with a binder (for example, sodium carboxymethyl cellulose, methyl cellulose, hydroxypropylmethyl cellulose, gelatin, polyvinyl pyrrolidone and polyvinyl alcohol), a dissolution retardant (for example, paraffin), a resorption promoter (for example, quaternary salt), or an adsorbent (for example, bentonite, kaolin and calcium diphosphate). The powdery composition can be granulated by wetting with a binder such as a syrup, starch glue, gum arabic, cellulose solution or polymer solution, followed by mixing with stirring, drying and grinding. Instead of the procedure for granulating a powder as described above, another procedure may be employed in which a mix is subjected first to a tablet compacting machine to form a morphologically incomplete slug which is then ground. A granule thus obtained may contain, as a lubricant, stearic acid, stearates, talc, mineral oil and the like, for the purpose of preventing any adhesion with each other. The mixture thus lubricated is then compacted into tablets. A plane tablet thus obtained may be film-coated or sugar-coated.

The compounds of the present invention may be mixed with a fluidized inert carrier and then compacted directly into tablets without being subjected to the granulating or slugging process described above. A transparent or semi-transparent protective film in the form of a shellac sealing film, a film of a sugar or polymeric material and a glossy film of a wax may also be employed. Other oral dosage forms, such as a solution, syrup and elixir can be formulated as a unit dosage form whose certain amount contains a certain amount of a medicament. Syrup is produced by dissolving the compounds of the present invention in a flavored aqueous solution, while an elixir is produced by using a non-toxic alcoholic carrier. A suspension is formulated by dispersing a compound in a non-toxic carrier. Additives such as a solubilizing agent, an emulsifier (for example ethoxylated isostearyl alcohols, polyoxyethylene sorbitol esters), a preservative and a flavor (for example, peppermint oil, saccharin) may also be added, if necessary.

An oral unit dosage formulation may be a microcapsule if desired. Such a formulation may also be coated or embedded in a polymer, wax or the like to obtain a prolonged activity or sustained release of the active ingredient.

In parenteral administration, an injection and a suppository can be used. Parenteral administration can be accomplished by using a liquid unit dosage form, such as a solution or suspension, for subcutaneous, intramuscular or intravenous administration. Such a unit dosage form can be produced by suspending or dissolving predetermined amount of the compound of the present invention in a non-toxic liquid carrier such as an aqueous or oily medium compatible with the purpose of the injection followed by sterilizing the suspension or solution. It is also possible to add a non-toxic salt or salt solution for the purpose of making an injection solution isotonic. It is also possible to use a stabilizer, preservative, emulsifier and the like.

A rectal administration can be accomplished by using a suppository or the like produced by suspending or dissolving the compounds of the present invention in a water-soluble or water-insoluble solid having a low melting point such as a polyethylene glycol, cocoa butter, semi-synthesized fats and fatty oils (for example, Witepsol (R)), higher esters (for example, myristyl palmitate) as well as a mixture thereof.

In the remedy for chronic rheumatoid arthritis of the present invention, it is possible to use in combination with other ingredients, for example, an anti-inflammatory steroid, a nonsteroid anti-inflammatory agent, an immunosuppressive agent, a disease-modifying antirheumatic drug and the like.

BEST MODE FOR CARRYING OUT THE INVENTION

The present invention will now be described in more detail with reference to Production Examples of typical starting materials (Reference Examples), Production Examples of the compounds of the present invention (Examples), Pharmaceutical Preparation Examples and Test Examples, but the present invention is not limited thereto. The specific rotation was measured at 20° C.

REFERENCE EXAMPLE 1

Production of (E)-2-(2-tert-butoxycarbonylaminoethoxy)-6-[2-(4-pyridyl)ethenyl]aniline (Step 1) Synthesis of 3-hydroxy-2-nitrobenzaldehyde 3.62 g of 3-methoxy-2-nitrobenzaldehyde was dissolved in 80 ml of methylene chloride and a boron tribromide-methylene chloride solution (15.03 g of, boron tribromide, 40 ml of methylene chloride) was added dropwise under ice cooling, followed by stirring at 0° C. for one hour. The reaction solution was poured into ice, extracted with chloroform, dried and then concentrated to obtain 3.32 g of the desired compound.

(Step 2) Production of (E)-2-acetoxy-6-[2-(4-pyridyl)ethenyl]nitrobenzene

To 3.17 g of the compound obtained in the step 1, 1.94 g of 4-picoline and 4.79 g of acetic anhydride were added, and then the mixture was refluxed with stirring for 12 hours. The reaction solution was poured into ice, neutralized with potassium carbonate, extracted with chloroform and then dried over magnesium sulfate. After the solvent was distilled off under reduced pressure, the residue was subjected to silica gel column chromatography ($CHCl_3$) to obtain 4.78 g of the desired compound.

(Step 3) Production of (E)-2-hydroxy-6-[2-(4-pyridyl)ethenyl]nitrobenzene 4.54 g of the compound obtained in the step 2 was dissolved in 160 ml of methanol and 4.42 g of potassium carbonate was added, followed by stirring at room temperature for 2 hours. After the reaction solution was concentrated, the residue was combined with iced water and neutralized with 2 N-hydrochloric acid and then the deposited powder was collected by filtration to obtain 3.47 g of the desired compound. The resulting compound was used as a material without further purification.

(Step 4) Production of (E)-2-(2-tert-butoxycarbonylaminoethoxy)-6-[2-(4-pyridyl)ethenyl]nitrobenzene 2.18 g of the compound obtained in the step 3 was dissolved in 9 ml of DMSO and 0.54 g of 60% sodium hydride was added under an argon gas flow, followed by stirring at room temperature for one hour. 4.63 g of 2-bromoethyl-tert-butoxycarbonylamine was added, followed by stirring with heating at 120° C. for 3 hours. The reaction solution was poured into iced water, combined with ethyl acetate, washed with water (3 times), washed with saturated brine and then dried over magnesium sulfate. After the solvent was distilled off under reduced pressure, the residue was subjected to silica gel column chromatography ($CHCl_3$:MeOH=50:1) to obtain 1.90 g of the desired compound.

(Step 5) Production of (E)-2-(2-tert-butoxycarbonylaminoethoxy)-6-[2-(4-pyridyl)ethenyl]aniline 1.90 g of the compound obtained in the step 4 was dissolved in 50 ml of 70% hydrous methanol and 4.90 g of reduced iron and 0.30 g of calcium chloride were added, and then the mixture was refluxed with stirring for 4 hours. After the reaction solution was filtered through celite, the filtrate was concentrated and the residue was subjected to silica gel column chromatography ($CHCl_3$:MeOH=50:1) to obtain 1.45 g of the desired compound.

EXAMPLE 1

(E)-4-[2-{2-[N-phenoxycarbonyl-N-(4-methoxybenzenesulfonyl)amino]phenyl}ethenyl]pyridine 1.00 g of (E)-4-[2-{2-[N-(4-methoxybenzenesulfonyl)amino]phenyl}ethenyl]pyridine was suspended in 40 ml of chloroform and, after adding 1.82 g of phenyl chlorocarbonate, 1.20 g of triethylamine was slowly added under ice cooling. Then, the mixture was stirred at room temperature for 5 minutes. The solvent was distilled off under reduced pressure and the desired product was purified by silica gel column (carrier: Wako Gel C200, developing solvent chloroform) to obtain the desired compound. The desired compound was treated with ethanol to obtain 0.71 g of a white granular crystal.

Elemental analysis (for $C_{27}H_{22}N_2O_5S$) Calcd. (%): H, 4.55; C, 66.65; N, 5.75 Found (%): H, 4.51; C, 66.44; N, 5.67

In the same manner, the following desired compounds were synthesized.

EXAMPLE 2

(E)-4-[2-{2-[N-methoxycarbonyl-N-(4-methoxybenzenesulfonyl)amino]phenyl}ethenyl]pyridine Elemental analysis (for $C_{22}H_{20}N_2O_5S$) Calcd. (%): H, 4.75; C, 62.25; N, 6.60 Found (%): H, 4.83; C, 61.97; N, 6.51

EXAMPLE 3

(E)-4-[2-{2-[N-ethoxycarbonyl-N-(4-methoxybenzenesulfonyl)amino]phenyl}ethenyl]pyridine Elemental analysis (for $C_{23}H_{22}N_2O_5S.1/5H_2O$) Calcd. (%): H, 5.11; C, 62.49; N, 6.34 Found (%): H, 5.09; C, 62.39; N, 6.34

EXAMPLE 4

(E)-4-[2-{2-[N-n-propoxycarbonyl-N-(4-methoxybenzenesulfonyl)amino]phenyl}ethenyl]pyridine hydrochloride Elemental analysis (for $C_{24}H_{24}N_2O_5S \cdot HCl \cdot 1/2H_2O$) Calcd. (%): H, 5.26; C, 57.88; N, 5.63 Found (%): H, 5.23; C, 58.12; N, 5.72

EXAMPLE 5

(E)-4-[2-{2-[N-n-butoxycarbonyl-N-(4-methoxybenzenesulfonyl)amino]phenyl}ethenyl]pyridine hydrochloride Elemental analysis (for $C_{25}H_{26}N_2O_5S \cdot HCl \cdot 1/2H_2O$) Calcd. (%): H, 5.51; C, 58.64; N, 5.47 Found (%): H, 5.47; C, 58.44; N, 5.49

EXAMPLE 6

(E)-4-[2-{3-(2-aminoethoxy)-2-[N-(4-methoxybenzenesulfonyl)amino]phenyl}ethenyl]pyridine dihydrochloride (Step 1) Production of (E)-4-[2-{3-(2-tert-butoxycarbonylaminoethoxy)-2-[N-(4-methoxybenzenesulfonyl)amino]phenyl}ethenyl]pyridine 1.42 g of (E)-2-(2-tert-butoxycarbonylaminoethoxy)-6-[2-(4-pyridyl)ethenyl]aniline obtained in the step 5 of Reference Example 3 was dissolved in 14 ml of pyridine and 0.99 g of 4-methoxybenzenesulfonyl chloride was added, followed by stirring at room temperature overnight. The reaction solution was concentrated and the residue was combined with iced water, extracted with chloroform and then dried over magnesium sulfate. After the solvent was distilled off under reduced pressure, the residue was subjected to silica gel column chromatography ($CHCl_3$:MeOH= 30:1) to obtain 2.19 g of the desired compound.

(Step 2) Production of (E)-4-[2-{3-(2-tert-butoxycarbonylaminoethoxy)-2-[N-(4-methoxybenzenesulfonyl)amino]phenyl}ethenyl]pyridine 1-oxide 0.56 g of the compound obtained in the step 1 was dissolved in 5 ml of chloroform and m-chloroperbenzoic acid was added, followed by stirring at room temperature for one hour. The reaction solution was washed with water three times and then dried over magnesium sulfate. After the solvent was distilled off under reduced pressure, the residue was subjected to silica gel column chromatography ($CHCl_3$:MeOH=20:1) to obtain 0.46 g of the desired compound.

(Step 3) 2.10 g of the compound obtained in the step 2 was dissolved in 10 ml of methylene chloride and 10.5 ml of trifluoroacetic acid was added dropwise under ice cooling, followed by stirring at room temperature for 2 hours. The reaction solution was combined with iced water, made weak basic by the addition of potassium carbonate, extracted with chloroform and then dried over magnesium sulfate. After the solvent was distilled off under reduced pressure, the residue was subjected to silica gel column chromatography ($CHCl_3$:MeOH=20:1) to obtain 1.33 g of a free form.

The free form was dissolved in 20 ml of methanol and an excess amount of a 20% hydrochloric acid-ether solution was added under ice cooling, followed by stirring for one hour. The reaction solution was concentrated and treated with ethanol to obtain 1.30 g of the desired compound (pale yellow crystal).

Elemental analysis (for $C_{22}H_{23}N_3O_4S \cdot 2HCl \cdot H_2O$) Calcd. (%): C, 51.17; H, 5.27; N, 8.14 Found (%): C, 51.04; H, 4.99; N, 8.02

EXAMPLE 7

(E)-4-[2-{3-(2-aminoethoxy)-2-[N-(4-methoxybenzenesulfonyl)amino]phenyl}ethenyl]pyridine 1-oxide dihydrochloride 2.38 g of the compound obtained in the step 2 of Example 6 was dissolved in 23 ml of methylene chloride and 23 ml of trifluoroacetic acid was added dropwise under ice cooling, followed by stirring at room temperature for 2 hours. The reaction solution was combined with iced water, made weak basic by the addition of potassium carbonate, extracted with chloroform and then dried over magnesium sulfate. After the solvent was distilled off under reduced pressure, the residue was subjected to silica gel column chromatography ($CHCl_3$:MeOH:28% $NH_3$(aq.)=90:10:1) to obtain 1.48 g of a free form.

The free form was dissolved in 50 ml of methanol and an excess amount of a 20% hydrochloric acid-ether solution was added under ice cooling, followed by stirring for one hour. The reaction solution was concentrated and treated with ethanol to obtain 1.50 g of the desired compound (pale yellow crystal).

Elemental analysis (for $C_{22}H_{23}N_3O_5S \cdot 2HCl \cdot 0.3H_2O$) Calcd. (%): C, 50.83; H, 4.96; N, 8.08 Found (%): C, 50.86; H, 4.88; N, 7.99

TEST EXAMPLE 1

Arthritis Inhibitory Effect

As described as followed, the inhibitory effect in arthritis of the compounds of the present invention could be confirmed by using type II collagen-induced arthritis as a model near to human chronic rheumatoid arthritis and using E)-4-{2-[2-{N-acetyl-N-[(4-methoxyphenyl)sulfonyl]amino}phenyl]ethenyl}pyridine 1-oxide (hereinafter referred to as a compound 1) as a test compound.

8-week-old DBA/1J male mice (7 to 10 mice) were used. 0.1 ml of an emulsion prepared by mixing a 0.1 M solution of acetic acid in physiological saline (2 mg/ml) of type II collagen derived from bovine joint cartilage and complete Freund's adjuvant at a mixing ratio of 1:1 was injected intradermally at the base of the tail in mice (primary sensitization). 21 days later, 0.1 ml of the emulsion prepared in the same manner as in case of primary sensitization was injected subcutaneously again at the back in mice (secondary sensitization). The test compound was suspended in an aqueous 0.5% methyl cellulose solution and administered orally to the mice once a day, which started from the primary or secondary sensitization. After 35 days from the primary sensitization, symptoms of arthritis was visually observed and the results were used a score of arthritis.

The results are shown in Table 1 and Table 2.

TABLE 1

Arthritis inhibitory effect in case administration of the test compound started from the primary sensitization

| Name of compound | Dosage (mg/kg) | Inhibition ratio (%) |
| --- | --- | --- |
| Compound 1 | 1 | −8.5 |
| Compound 1 | 5 | 69.5* |

*$P < 0.05$,
**$P < 0.01$ (Wilcoxon's rank sum test)

TABLE 2

Arthritis inhibitory effect in case administration of the
test compound started from the secondary sensitization

| Name of compound | Dosage (mg/kg) | Inhibition ratio (%) |
| --- | --- | --- |
| Compound 1 | 5 | 69.6* |
| Compound 1 | 10 | 100.0** |

*$P < 0.05$,
**$P < 0.01$ (Wilcoxon's rank sum test)

As is apparent from the above tables, the compound 1 exerted a significant inhibitory effect at a dosage of 5 mg/kg in case administration of the test compound started from the primary sensitization, or 5 and 10 mg/kg in case administration of the test compound started from the secondary sensitization. Namely, the compound 1 exerts a collagen-induced arthritis inhibitory effect even in the administration schedule after the secondary sensitization and is also useful as a remedy for chronic rheumatoid arthritis.

TEST EXAMPLE 2

Acute Toxicity 7-week-old $CDF_1$ male mice (6 mice) were used. The compound 1 was suspended in 0.5% methylcellulose and the resulting suspension was orally administered once by oral probe. The mortality rate was investigated after 2 weeks and the $LD_{50}$ value was calculated by the probit method. As a result, the $LD_{50}$ value of the compound 1 was found to be 620.5 mg/kg and the compound 1 had very low toxicity.

The above results indicate clearly that the compounds of the present invention have very low toxicity and high safety. The results of Test Examples 1 and 2 indicate clearly that the compounds of the present invention have excellent inhibitory effect on type II collagen-induced arthritis and low toxicity.

FORMULATION EXAMPLE 1

180 mg Per Tablet for Internal Use

| | |
| --- | --- |
| Compound 1 | 10 mg |
| Lactose | 100 mg |
| Corn starch | 55 mg |
| Low substituted hydroxypropyl cellulose | 9 mg |
| Polyvinyl alcohol (partially saponified product) | 5 mg |
| Magnesium stearate | 1 mg |

The above ingredients are weighed in accordance with the formulation. The ingredients, excluding polyvinyl alcohol and magnesium stearate, are uniformly mixed and tabletting granules are produced by a wet granulation method using an aqueous polyvinyl alcohol solution as a binder. After mixing the tabletting granules with magnesium stearate, the mixture is subjected to a tablet compacting machine to mold into tablets each 8 mm in diameter weighing 180 mg per tablet, thereby obtaining a tablet for internal use.

FORMULATION EXAMPLE 2

220 mg Per Hard Capsule

| | |
| --- | --- |
| Compound 1 | 10 mg |
| Lactose | 187 mg |
| Microcrystalline cellulose | 20 mg |
| Magnesium stearate | 3 mg |

The above ingredients are weighed in accordance with the formulation and, after mixing uniformly, 220 mg of the mixture is filled into a #2 capsule by using a capsule-filling machine, thereby obtaining a hard capsule.

FORMULATION EXAMPLE 3

1 g Per Granule

| | |
| --- | --- |
| Compound 1 | 10 mg |
| Lactose | 880 mg |
| Low substituted hydroxypropyl cellulose | 70 mg |
| Hydroxypropyl cellulose | 40 mg |

The above ingredients are weighed in accordance with the formulation and, after mixing and kneading uniformly, the kneaded mixture is subjected to a granulating machine to mold into granules each 0.7 mm in diameter, thereby obtaining a granule.

FORMULATION EXAMPLE 4

1 ml Per Injection

| | |
| --- | --- |
| Compound 2 | 10 mg |
| Mannite | 50 mg |
| Water for injection | q.s. |

(Compound 2 is (E)-4-{2-[2-{N-(4-methoxybenzenesulfonyl)-N-[4-(2-pyridyl)piperadino]acetylamino}phenyl]ethenyl}pyridine 1-oxide dihydrochloride)

Preparation Method

After the compounds of the present invention and mannite are dissolved in water for injection, the resulting solution is aseptically filtered through a membrane filter (pore size: 0.22 μm). After filling into a vial, the vial is subjected to freeze-drying to obtain an injection to be dissolved before use.

FORMULATION EXAMPLE 5

1 ml Per Injection

| | |
| --- | --- |
| Compound 2 | 10 mg |
| Maltose | 100 mg |
| Water for injection | q.s. |

Preparation Method

After the compounds of the present invention and maltose are dissolved in water for injection, the resulting solution is aseptically filtered through a membrane filter (pore size:

0.22 μm). After filling into a vial, the vial is subjected to freeze-drying to obtain an injection to be dissolved before using.

INDUSTRIAL APPLICABILITY

Since the compounds of the present invention have an intense arthritis inhibitory effect in a dose, which is by far lower than the dose enough to exhibit an anticancer activity, and can be administered orally, they can be safely used as a remedy for juvenile rheumatoid arthritis, Reiter's syndrome and SLE, Behcet's syndrome, in addition to chronic rheumatoid arthritis.

What is claimed is:

1. A method of treating chronic rheumatoid arthritis, comprising administering to a subject in need of such a therapeutically effective amount for the treatment of rheumatoid arthritis of a composition comprising an aminostilbazole derivative represented by the following formula or salt thereof as an active ingredient:

A-B-D-E  [1]

wherein A represents optionally substituted pyridyl or an oxide thereof, B represents optionally substituted ethenylene, D represents optionally phenylene, E represents the following formula:

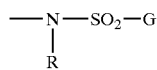

wherein G represents optionally substituted phenyl, R represents (1) hydrogen, (2) optionally substituted alkyl, (3) optionally substituted alkenyl, (4) alkynyl, or (5) —COR°, R° represents alkyl, alkoxy, aryloxy.

2. The method for treating chronic rheumatoid arthritis according to claim 1, wherein A is optionally substituted pyridyl or 1-oxide pyridyl, B is non-substituted ethenylene, D is non-substituted or aminoalkoxy-substituted 1,2-phenylene, R of —N(R)—SO$_2$—G as E is alkyl which may be substituted with a substituent selected from the group consisting of halogen, amino, monoalkylamino, dialkylamino, morpholino, alkoxy, hydroxy, cyano, the formula: —CONR$^1$R$^2$ (wherein R$^1$ and R$^2$ are the same or different and each represents hydrogen, hydroxy, alkyl, alkoxy, cycloalkyl, cycloalkyloxy, aryl, aryloxy, aralkyl, aralkyloxy, cycloalkylalkyl, cycloalkylalkyloxy, or tetrahydrofurnnyloxy), and the formula: —SO$_2$NR$^3$R$^4$ (wherein R$^3$ and R$^4$ are the same or different and each represents hydrogen or alkyl), alkenyl which may be substituted with halogen, or —COR°, R° is alkyl, and G is 4-alkoxyphenyl.

3. The method for treating chronic rheumatoid arthritis according to claim 1, wherein A is non-substituted 4-pyridyl or 1-oxide-4-pyridyl, B is ethenylene of a non-substituted trans form, D is non-substituted or aminoalkoxy-substituted 1,2-phenylene, R of —N(R)—SO$_2$—G as E is hydrogen, hydroxyalkyl or —COR°, R° is alkyl, and G is 4-methoxyphenyl.

4. The method for treating chronic rheumatoid arthritis according to claim 1, wherein the compound represented by the formula [I] is a compound selected from the group consisting of (E)-4-[2-{2-[N-acetyl-N-(4-methoxybenzenesulfonyl)amino]phenyl}ethenyl]pyridine 1-oxide, (E)-4-[2-{2-[N-4-acetyl-N-(4-methoxybenzenesulfonyl)amino]phenyl}ethenyl]pyridine (E)-4-[2-{2-[N-(4-methoxybenzenesufonyl)amino]phenyl}ethenyl]pyridine 1-oxide, (E)-4-[2-{2-[N-(4-methoxybenzenesulfonyl)amino]phenyl}ethenyl]pyridine, (E)-4-[2-{2-[N-(2-hydroxyethyl)-N-(4-methoxybenzenesulfonyl)amino]phenyl}ethenyl]pyridine 1-oxide, (E)-4-[2-{2-(2-aminoethyloxy)-2-[N-(4-methoxybenzenesulfonyl)amino]phenyl}ethenyl]pyridine and (E)-4-[2-{3-(2-aminoethyloxy)-2-[N-(4-methoxybenesulfonyl)amino]phenyl}ethenyl]pyridine 1-oxide.

5. The method of claim 1, wherein the composition is administered orally or parenterally to the subject.

6. The method of any one of claims 1 to 4 wherein the treatment alleviates pain in a joint and relieves inflammation in the joint.

7. The method of any one of claims 1 to 4 wherein the treatment maintains or repairs a joint function to prevent breakage of bone and cartilage.

8. The method of any one of claims 1 to 4 wherein the composition is administered in combination with an anti-inflammatory steroid, a nonsteroid anti-inflammatory agent, an immunosuppressive agent, or antirheumatic drug.

* * * * *